United States Patent [19]

Lindroos

[11] 4,431,581
[45] Feb. 14, 1984

[54] HEME CONCENTRATE AND METHOD FOR THE PREPARATION THEREOF

[76] Inventor: Paul G. S. Lindroos, Eriksgatan 37, 20100 Åbo 10, Finland

[21] Appl. No.: 324,395
[22] PCT Filed: Apr. 1, 1981
[86] PCT No.: PCT/FI81/00026
§ 371 Date: Nov. 16, 1981
§ 102(e) Date: Nov. 16, 1981
[87] PCT Pub. No.: WO81/02834
PCT Pub. Date: Oct. 15, 1981

[30] Foreign Application Priority Data

Apr. 3, 1980 [SE] Sweden ................................ 8002591

[51] Int. Cl.$^3$ .......................... A23J 1/06; C07G 7/00; C07C 103/52
[52] U.S. Cl. .......................... 260/112 B; 260/112.5 R; 424/101; 426/647; 426/657
[58] Field of Search ...................... 260/112.5 R, 112 B

[56] References Cited

U.S. PATENT DOCUMENTS

4,098,780 7/1978 Lindroos .......................... 426/647 X
4,330,463 5/1982 Luijerink .......................... 260/112

FOREIGN PATENT DOCUMENTS

7715575 7/1976 Australia .
2526596 1/1976 Fed. Rep. of Germany .
2656157 6/1977 Fed. Rep. of Germany .

OTHER PUBLICATIONS

International J. of Biochemistry, vol. 4, No. 21 (1973), pp. 259–267, Wakid et al.
Journal of Histochemistry and Cytochemistry, vol. 22, No. 9 (1974), pp. 908–910, Straus.
The Proteins, vol. II, Part A, pp. 328–329.
Acta Med. Scand. Suppl. 629, 1980, Reizenstein, pp. 7–47.
Organic Chemistry, 1951, Holliman, p. 529.
Handbook of Chemistry & Physics, p. 170.
Porphyrins & Metalloporphyrns, pp. 829–833, Smith
Nutrition Reports International, May, 1976, vol. 13, p. 330.
Textbook of Biochemistry, West et al., pp. 493 & 500.
Practical Physiological Chem., Hawk et al., 1954, p. 469.

Primary Examiner—Howard E. Schain
Attorney, Agent, or Firm—Lerner, David, Littenberg, Krumholz & Mentlik

[57] ABSTRACT

A heme concentrate containing 15 to 55 percent heme in readily absorbable form and useful as a pharmaceutical against anemia and as an iron-enriching agent in foodstuffs, and a method for the preparation of said heme concentrate of a mixture of heme and blood substance obtained when cleaving hemoglobin, for example, from whole blood or red blood cells, by treating said mixture with a dehydrating agent, preferably a lower alcohol or a mixture of alcohols, either at a pH of at least 8.0 or in the presence of a substance promoting the separation, preferably imidazole or an imidazole derivative, at a pH of at least 6.0, preferably 6.5 to 8.5, whereafter the solid blood substance is separated and the heme concentrate is recovered from the remaining solution; the blood substance simultaneously recovered, mainly globin, is intended for purposes of foodstuffs and fodder.

17 Claims, 2 Drawing Figures

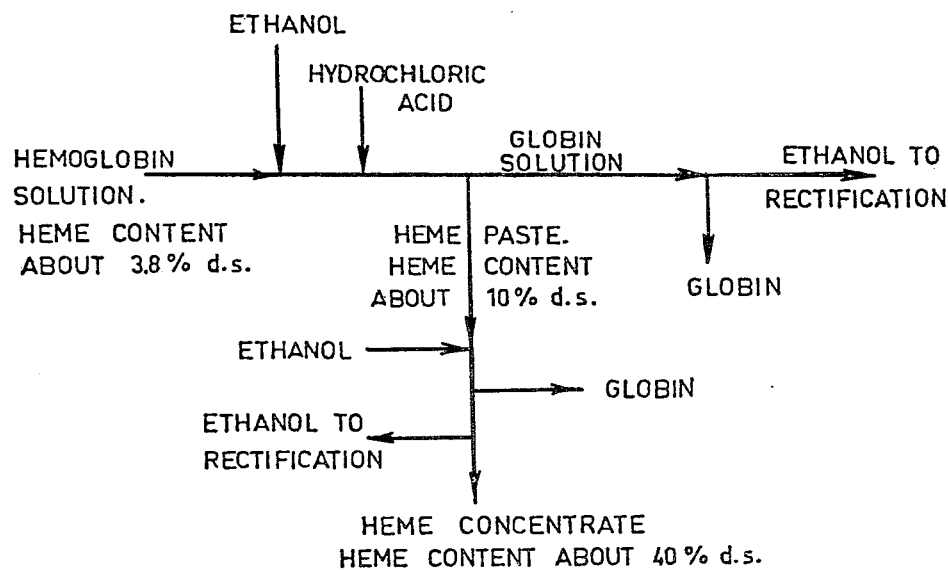
FIG. 1 ETHANOL METHOD
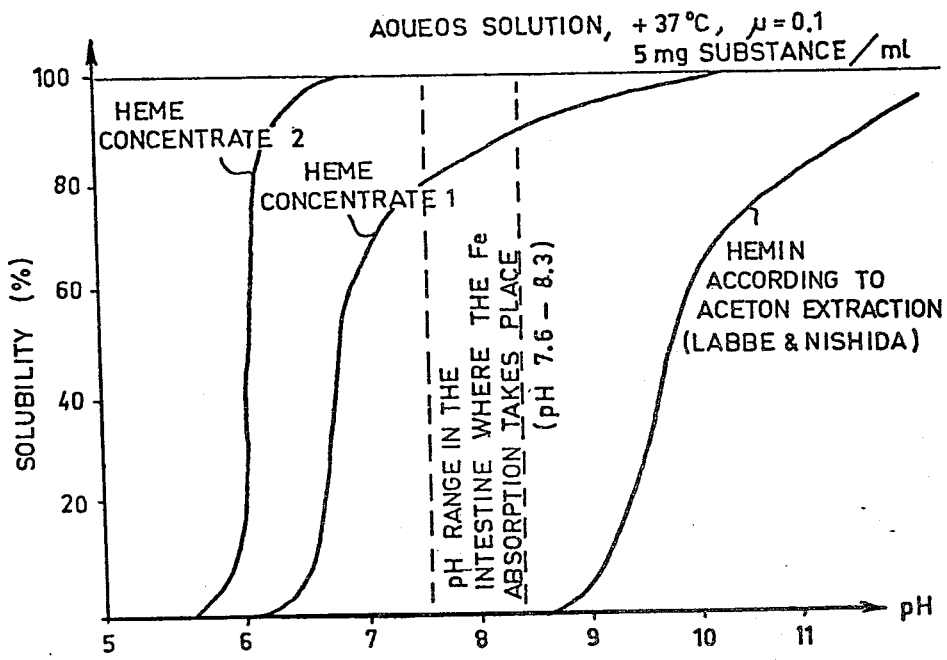
FIG. 2 SOLUBILITY OF HEME CONCENTRATE AND HEMIN ACCORDING TO ACETONE EXTRACTION

HEME CONCENTRATE AND METHOD FOR THE PREPARATION THEREOF

Slaughtering blood contains baluable components, namely protein having a high nutritive value and functional properties, which make it useful as texturing agent in foodstuffs, and further heme which is a sought-after iron-enriching agent.

The hemoglobin, which contains the main part of the protein in the blood, has a taste of iron because of the heme. It is therefore of interest to develop a method for cleaving the hemoglobin into an iron-free globin and a heme concentrate, and in such a way that the functional properties of the protein and the heme are preserved so as to give these products a high value.

As is well-known, protein is easily denatured and therewith looses its functional properties, for example, when treated at a high pH (over 9 to 10). The denaturation can be counteracted by operating at a low temperature, less than 0° C.

In order that heme may be useful as a pharmaceutical, i.e. in order that the iron be present in a readily absorbable form, the heme must be present in native form. In hemoglobin, the heme is present in native form out of which the iron, as krown, is readily absorbed.

Out of conventional iron preparations, such as iron sulfate, only a fraction of the iron is absorbed because certain substances present in the food (e.g., phytates) prevent the absorption. This drawback is not present in iron based on heme.

Heme has a pronounced tendency to polymerize and to form difficultly soluble aggregates out of which the iron cannot be absorbed. Known methods for cleaving the hemoglobin into heme and globin and for separating the heme by extraction with acetone or methyl ethyl ketone result in a polymerized heme.

The present invention realtes to a method for recovering a heme concentrate from a mixture of heme and blood substance obtained when cleaving hemoglobin.

Heme, iron heme, is composed of iron and protoporphyrin (see, for example, Textbook of Biochemistry, West & Todd, MacMillan Co., 1961, p. 533) and constitutes the prosthetic group in hemoglobin and amounts to 3.8 percent by weight based on the hemoglobin.

As starting material, a heme product is preferably used which is obtained by cleaving hemoglobin into heme and globin.

The cleavage can be carried out in different ways, for example, by treating hemoglobin in an acid or alkaline milieu.

The raw material can comprise, for example, whole blood, red blood cells, or hemoglobin in another milieu.

A particularly suitable starting material is the heme product obtained according to the method described in the Swedish Patent No. 7407882-5 and in the Swedish Patent Application No. 7513987-3. According to this method, the hemoglobin is cleaved in an aqueous ethanol solution having an ethanol content of at least 40 percent by volume, at a pH of less than 4.5. The precipitate of heme product formed thereby is separated. The remaining globin solution is practically free of heme.

This known product contains about 10 percent by weight of heme while the rest consists of other blood substance, most likely mainly of protein. Moreover, this heme product, in all probability, contains blood substances, such as lipoproteins, lipides, phosphatidyl compounds and cholesterol.

According to the new method, a heme concentrate is obtained having a heme content of about 40 percent by weight. The composition is not known. This heme concentrate is intended for use as a pharmaceutical against anemia and and as an iron-enriching agent in foodstuffs.

The blood protein, mainly globin, which is simultaneously recovered, is intended for purposes of foodstuffs and fodder.

The method is technically and economically feasibly on industrial scale.

According to the method according to the invention, said heme raw material is treated with a dehydrating agent, preferably a lower alcohol or a mixture of alcohols and/or ketones and esters, said treatment taking place either (a) at a pH of at least 8.0, preferably 9.0 to 10.5, or (b) in the presence of a compound of the formula:

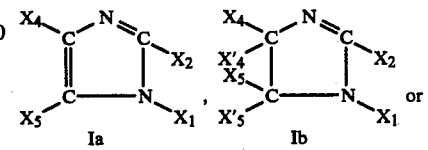

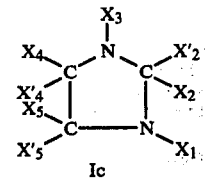

where the substituents can have the following meanings:

—R (R is a saturated or unsaturated alkyl or aryl or CH$_3$) —H,

—R (R)$_n$, —COOH, —R(COOH)$_n$, —COOR, —R(COOR)$_n$,

—OH, —ROH, —R(OH)$_n$, —R(OH)$_n$R,

—OR, —ROR, —R(OR)$_n$,

—NH$_2$, —R(NH$_2$)$_n$, —NR$_2$, —RNR$_2$, —N$_2$R,

—CN, —R(CN)$_n$,

—Cl, —R(Cl)$_n$, —F, —R(F)$_n$, —Br, —R(Br)$_n$, —J, —R(J)$_n$,

—NO$_2$, —R(NO$_2$)$_n$,

—COR, —R(COR)$_n$, —R(COCOOH)$_n$, —R(COCOOR)$_n$, —OCOR,

—SH, —R(SH)$_n$, —SR, —R(SR)$_n$, —S—S—, —S—C-S—S—, —SO$_2$H, —SO$_3$H,

—RNHCOOH, —RNHCOOR, —R(NH)$_n$R(OH)$_n$, —R(NHCOR)$_n$COOH, —R(NHCOR)$_n$COOR,

—NHCOOH, —NHCOOR, —R(NHCOOH)$_n$, —R(NHCOOR)$_n$, —R(NH$_2$)$_n$(COOH)$_n$,

—R(NH$_2$)$_n$(COOR)$_n$, —R(COOH)$_n$NHCOOH, —R(COOR)$_n$NHCOOR, —RN(R)ROH,

—R[R(NH$_2$)$_n$OH]$_n$,

—CONH$_2$, —R(CONH$_2$)$_n$, —CONHNH$_2$, —R(CONHNH$_2$)$_n$, —NHCONH$_2$, —R(NHCONH$_2$)$_n$,

—NHCOR, —RNHCOR, —CONHR, —RCONHR, —CON$_3$, —R(CON$_3$)$_n$, —RCOOHNHCORNH$_2$,

—SO$_2$NHR, —SO$_2$RNHCOOR, —CONHNHSO$_2$R, —RSO$_2$R,

—NHNO$_2$, —RONO$_2$,

—RClCOOH, —RClCOOR, —RFCOOH, —RFCOOR, —RBrCOOH, —RBrCOOR,

—RJCOOH, —RJCOOR, and where, in addition, X$_4$ and X', and/or X$_5$ and X$_5$', can be substituted (replaced) by =O, =NH, =S, =CHR(NO₂)ₙ, =N(H₂PO₄) or =CHR, and for the imidazoline compound Ib, in addition, X₄ and X₄' and/or X₅ and X₅', and for the imidazoline compound Ic, moreover, X₂ and X₂', X₄ and X₄', and/or X₅ and X₅', also can be substituted by =O, =NH, =S, =CHR(NO₂)ₙ, =N(H₂PO₄) and =CHR, in which substituent formulas n is a number from 1 to 5, or any other similar compound, such as:

Anserine

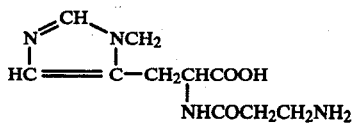

Carnosine

Ergotioneine

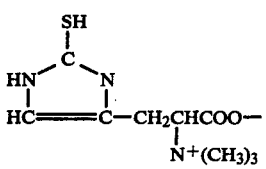

Histamine    Imidazolyl—CH₂CH₂NH₂
Histidole    Imidazolyl—CH₂CH₂OH
Dimethylhistamine Histidine

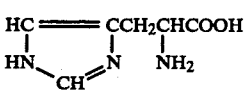

Pilocarpine

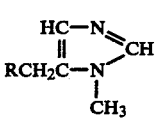

Pilosinine

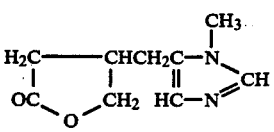

Thiolhistidine

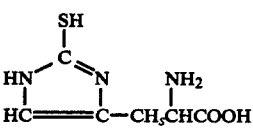

Hercynine    

Imidazolyl glycine [imidazolyl-CH(NH₂)COOH]
Imidazolyl lactic acid (imidazolyl-CH₂CHOHCOOH)
Imidazolyl propionic acid (imidazolyl-CH₂CH₂COOH)
Urocanic acid (imidazolyl-CH=CHCOOH)
Histamine-tyramine (HOC₆H₄CH₂CH₂NHCH₂CH₂-imidazolyl)
Imidazolyl acidic acid (imidazolyl-CH₂COOH)

Sulfaimidazoles

Vitimidazole

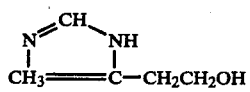

Sulfaimidazoles
Thiolhistamine

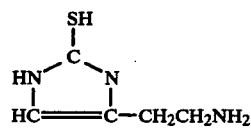

at a pH of at least 6.0, preferably 6.5 to 8.5 whereafter the undissolved blood substance is separated, e.g., by centrifugation or filtration and the heme concentrate is precipitated from the remaining solution by lowering pH to a value less than 6.5, and is recovered.

It is previously known to cleave hemoglobin into heme and globin in an alkaline milieu while extracting the heme, for example, in acetone or methyl ethyl ketone to separate it in this way from the globin. This extraction is carried out in 100% acetone to give a pure heme without any other blood substance. However, this heme has proved to polymerized and has a poor solubility (see FIG. 2).

From the Swedish Patent Publication No. 76-00020-7 it is known to prepare an iron preparation based on hemoglobin by linking iron porphyrin to hemoglobin or globin at a pH of 8 to 9.

According to the new method, the heme concentrate is separated from any other blood substance, i.e. mainly protein, so that the heme concentrate is converted into the dissolved form while the remaining substance is present in undissolved form.

Suitable extraction agents are ethanol, methanol, propanol, isopropanol, butanol, isobutanol, ethylene glycol, and glycerol. Ethanol is preferred because it is not toxic.

The content of extraction agent must be over 40 percent by weight, preferably over 60 percent by weight.

The pH value must, in the presence of a compound of the formula I, be at least 6.0, preferably 6.5 to 8.5. Otherwise, the pH value must be at least 8.0, preferably 9.0 to 10.5

In order to prevent denaturation of the protein the temperature is maintained low, preferably less than $-5°$ C.

The temperatur does not affect the reaction, only the degree of denaturation of the protein.

In order to prevent dissolution of blood substance from the heme/blood substance mixture simultaneously with the heme concentrate in the extraction solution, the blood substance, mainly globin, can be precipitated before the extraction. The precipitation can be effected, for example, by adjusting the pH for the mixture to a value of 7 to 8, the isoelectric pH range for globin, and/or by adding various salts. Suitable salts are, for example, Na, K, NN₄ chloride, sulphate, citrate, phosphate, tartrate.

The addition of salt has the conventional salting-out effect on proteins but has no special effect on the dissolution of the heme concentrate.

The addition of salt mainly comes into question when the extraction is carried out on a heme mixture from which the globin portion has not been previously separated.

In addition, other agents promoting the separation can be added, such as amino acid, e.g., glycine, glutamine, or lysine.

Glycine has the effect of increasing the yield of heme concentrate up to about 99 percent, see Example 8, when the other conditions at the same time are ideal.

Without the addition of glycine, the yield remains at about 93 to 95 percent.

The undissolved substance is separated, for example, by centrifugation or filtration.

The heme concentrate is precipitated out of the remaining solution, i.e. the supernatant or the filtrate, by lowering the pH value to less than 6.5, preferably 4.0 to 6.0. A black, flaky precipitate is then formed. The precipitation will be more quantitative when the pH value is less than 5.

The precipitation is rather undependent on the temperature, but in order to obtain a more quantitative precipitation and in order to subject the concentrate to a careful treatment, the precipitation is preferably carried out at a temperature of less than 0° C.

The pH is lowered, for example, with 0.1 M HCl. The precipitate is separated, for example, by centrifugation or filtration, and is washed free of ethanol, salt and imidazole with ice water.

The precipitate is dissolved in water by raising the pH, for example, to 8, and the solution can be freezed and freeze dried.

The yield of heme out of the extraction solutions amounts to about 90 percent.

Because the separation of heme concentrate can be carried out at a pH of less than 10.5 and at a temperature lower than 0° C., the protein is recovered in a nondenatured or an only partially denatured form whereby the functional properties thereof are preserved. In connection with foodstuffs, it is important to aim at proteins with texturing properties. The protein will be particularly satisfactory when recovered at a pH lower than about 9.

The heme concentrate obtained in the method according to the invention usually has a heme content of about 35 to 40 percent; in special cases, products having a lower (15 percent) and also a higher (up to 55 percent) heme content can be obtained.

The heme concentrate possibly is a new chemical compound consisting of heme and blood substance. The composition of the portion herein referred to as "blood substance" is not known. The heme concentrate cannot be physically split into its components, e.g., by gel filtration. Obviously, the compound is formed under the conditions prevailing when the heme is cleaved from the hemoglobin. In an aqueous ethanol solution having an ethanol content of more than 40 percent by volume and pH values higher than 6.0, this compound is freed from other blood substance. Since the solubility is good, it is easily separated from other blood substance which is not soluble under these conditions.

The presence of a compound of the formula I, such as imidazole, imidazoline, or imidazolidine, or a derivative thereof, facilitates the separation of the heme concentrate from adhering blood substance so that quantitative separation can be effected already at a pH value of 7.

The good solubility of the heme concentrate indicates that the heme is present in native form, not polymerized. Therefore, it is possible for the iron to be absorbed out of the heme concentrate, and it can then be used as an iron-enriching agent in foodstuffs and as a pharmaceutical against anemia.

THE SOLUBILITY OF THE HEME CONCENTRATE

FIG. 2 illustrates the solubility of the heme concentrate at different pH values. The heme concentrate 1 is representative of the product prepared according to the invention.

When treating the concentrate with a proteolytic enzyme, e.g., with trypsin, the concentrate is cleaved into smaller units and the solubility is somewhat improved; the heme concentrate 2 elucidates this.

For the sake of comparison, the solubility curve for hemin has been plotted (prepared by Nishida, Porphyrins and Metalloporphyrins, Kevin M. Smith, 1975, page 809).

As mentioned earlier, the heme preparation must be soluble at a pH value which is lower than or equal to the pH value, 7.5 to 8.2, which prevails in the intestine where the absorption of iron takes place.

THE ABSORPTION OF IRON OUT OF THE HEME CONCENTRATE

The absorption of iron was determined by means of clinical experiments.

To ten test persons was served an aqueous solution of heme concentrate marked with the isotope $^{55}$Fe. As a substance of comparison was used blood marked with the isotope $^{59}$Fe.

The absorbed iron quantity was determined by means of radioactive measurement. The results are presented in Table I.

The results show that the absorption of iron out of the heme concentrate was approximately of the same order, often even somewhat higher, than out of blood. This can be interpreted so that the heme concentrate exists in native form, which is the prerequisite for an absorption of iron.

TABLE I

| | | | | | | Absorption (%) | | Absorbed quantity (mg) | | |
|---|---|---|---|---|---|---|---|---|---|---|
| Test person male/female | Age (years) | Height (cm) | Weight (kg) | Hemoglobin value (g %) | Hct (%) | Blood | Heme concentrate | Blood | Heme concentrate | |
| f | 26 | 162 | 55 | 13,2 | 40 | 15,5 | 12,3 | 0,78 | 0,62 | 23,2 |
| m | 33 | 179 | 69 | 13,8 | 45 | 8,3 | 7,7 | 0,41 | 0,39 | 30,8 |
| f | 37 | 164 | 49 | 14,2 | 44 | 8,1 | 8,6 | 0,41 | 0,43 | 32,7 |
| f | 30 | 165 | 58 | 13,2 | 42 | 5,3 | 5,6 | 0,27 | 0,28 | 32,1 |
| m | 36 | 170 | 69 | 15,3 | 48 | 7,0 | 6,8 | 0,35 | 0,34 | 46,9 |
| m | 33 | 181 | 80 | 15,6 | 49 | 8,5 | 8,7 | 0,43 | 0,44 | 73,0 |
| m | 24 | 183 | 76 | 14,9 | 48 | 13,3 | 13,5 | 0,67 | 0,68 | 92,4 |
| m | 34 | 180 | 86 | 14,3 | 42 | 6,4 | 10,9 | 0,32 | 0,55 | 68,0 |
| m | 26 | 184 | 90 | 14,7 | 45 | 11,1 | 16,3 | 0,56 | 0,82 | 70,6 |
| m | 30 | 176 | 73 | 14,0 | 44 | 6,6 | 10,8 | 0,33 | 0,54 | 37,8 |
| Mean value: | | | | | | 9,0 | 10,1 | 0,45 | 0,51 | 50,8 |
| SEM: | | | | | | 1,04 | 1,04 | 0,05 | 0,05 | 7,40 |
| Absorbed quantity (mg) for a person who normally absorbs 40% of a standard | | | | | | | | 0,35 | 0,40 | |

TABLE I-continued

The absorption of iron out of heme concentrate

| Test person male/female | Age (years) | Height (cm) | Weight (kg) | Hemo-globin value (g %) | Hct (%) | Absorption (%) | | Absorbed quantity (mg) | |
|---|---|---|---|---|---|---|---|---|---|
| | | | | | | Blood | Heme concentrate | Blood | Heme concentrate |
| dose of iron preparation | | | | | | | | | |

EXAMPLE 1

A mixture of 4 ml of 96%-by-volume ethanol and 0.8 ml of 1 M HCl at a temperature of −8° C. was added dropwise, while stirring and cooling, to 2.2 g of a mixture of blood cells at a temperature of −5° C. After the addition, the pH value was 3.1 and the temperature −5° C. 3 ml of ice water and 1.8 ml of 0.5 M NaOH in 70%-by-volume ethanol was added while stirring and cooling; the temperature of the mixture was −5° C. and the pH 7.5. After 5 minutes, 10 ml of 96%-by-volume ethanol, 10 ml of 70%-by-volume ethanol, 1 ml of 1 M glycine in an aqueous solution and 2.2 ml of 0.5 M NaOH were added to the mixture while stirring and cooling. The mixture now contained 67%-by-volume ethanol, the pH was 10.3 and the temperature −5° C. The mixture was centrifuged at 3000×g for 5 minutes, whereby 38 ml of a red supernatant and a brownish red paste were obtained. The supernatant contained 0.18 mg of heme/ml (61.5% of the heme content of the starting material). The paste was mixed in 10 ml of 70%-by-volume ethanol at a temperature of −5° C., the pH was adjusted to 10.3, and the mixture was centrifuged as above. The supernatant contained 0.13 mg of heme/ml (11.7% of the heme content of the starting material). The paste was treated for a third time in the same manner as above, whereby 0.06 mg of heme/ml (5.4% of the heme content of the starting material) was obtained. The total yield of heme concentrate was 78.6%. The paste was brown and weighed in dry condition 0.27 g (protein yield 79.5%).

The above mentioned mixture of blood cells can be obtained in the following manner.

Slaughtering blood, with sodium citrate as anticoagulant, was separated by centrifugation, whereby plasma and a broth of red blood cells were obtained. Sodium chloride and ethanol were added to the broth of blood cells so that 2.2 g of the mixture of blood cells contained 0.34 g protein, 0.16 g sodium chloride, 0.26 g of 100% ethanol. and 1.44 g water, and soluble substances present in the blood. The protein, mainly hemoglobin, was determined by means of precipitation with ethanol. 2.2 g of the mixture of blood cells contained 11.1 mg hemin, determined according to the pyridine method.

EXAMPLE 2

In the same way as in Example 1, the pH was lowered to 3.1 and thereafter adjusted to 7.5. The mixture was extracted in the same way as in Example 1 but, in addition, by adding 1 ml of 2 M imidazole in 70%-by-volume ethanol. The pH was adjusted to 8.4. The supernatants contained 79%, 12% and 4%, respectively, of the heme content of the starting material. The total yield of heme concentrate was 95%. The paste was light brown and represented 85% of the protein content of the starting material.

EXAMPLE 3

A mixture of 2 ml water and 0.7 ml of 1 M HCl at a temperature of +1° C. was added dropwise, while stirring and cooling, to 2.2 g of a mixture of blood cells at a temperature of −8° C. After the addition, the pH was 3.2 and the temperature −5° C. 4 ml of 96%-by-volume ethanol, 10 ml of 70%-by-volume ethanol, 1 ml of 1 M glycine in an aqueous solution, 1 ml of 2 M imidazole in 70%-by-volume ethanol and 1.5 ml of 0.5 M NaOH in 70%-by-volume ethanol were added, while stirring and cooling; the temperature of the mixture was −5° C. and pH 8.0, the ethanol content was about 56%-by-volume. The mixture was centrifuged after 5 minutes as in Example 1 and yielded a supernatant containing 59% of the heme content of the starting material and a brown paste. The paste was extracted two times with 10 ml of 70%-by-volume ethanol, each time at a pH of 8.0, and yielded supernatants containing 18% and 8%, respectively, of the heme content of the starting material. The total yield of heme concentrate was 85%. The paste was brown and represented 72% of the protein content of the starting material.

EXAMPLE 4

A mixture of 3 ml of 96%-by-volume ethanol and 0.35 ml of 0.5 M NaOH in 70%-by-volume ethanol at a temperature of −10° C. was added dropwise, while stirring and cooling, to 2.2 g of a mixture of blood cels at a temperature of −10° C. After the addition, the pH was 10.2 and the temperature −10° C. A mixture of 2 ml of ice water, 3 ml of 50%-by-volume ethanol and 0.15 ml of 1 M HCl, at a temperature of −10° C. were added. The pH of the mixture was now 7.5 and the temperature −10° C. A mixture of 5 ml of 96%-by-volume ethanol, 5 ml of 70%-by-volume ethanol and 2 ml of 0.5 M NaOH in 70%-by-volume ethanol, at a temperature of −10° C. were added. The pH of the mixture was 10.3, the temperature −10° C., and the ethanol content about 64%-by-volume. The mixture was centrifuged after 5 minutes as in Example 1 and yielded a supernatant containing 46% of the heme content of the starting material and a dark brown paste. The paste was extracted twice with 10 ml of 65%-by-volume ethanol, each time at a pH of 10.3 and a temperature of −10° C., and yielded supernatants containing 14% and 7%, respectively, of the heme content of the starting material. The total yield of heme concentrate was 67%. The paste was brown and represented 71% of the protein content of the starting material.

EXAMPLE 5

In the same way as in Example 4, the pH of the mixture of blood cells was raised to 10.2, the temperature was maintained at 0° C. A mixture of 1.5 ml of ice water, 3 ml of 50%-by-volume ethanol, 1 ml of 2 M imidazole in 70%-by-volume ethanol and 0.2 ml of 1 M HCl, at a temperature of 0° C. was added. The pH of the mixture was 8.2 and the temperature 0° C. Hereafter a mixture of 5 ml of 96%-by-volume ethanol and 10 ml of 70%-by-volume ethanol, at a temperature of 0° C. were added. The pH of the mixture was 8.2, the temperature 0° C., and the ethanol content 66% by volume. The mixture was centrifuged after 5 minutes as in Example 1 and yielded a supernatant containing 52% of the heme content of the starting material and a dark brown paste. The paste was extracted twice with 10 ml of 65%-by-volume ethanol and 0.2 ml of 2 M imidazole in 70%-by-volume ethanol, each time at a pH of 8.2 and a temperature of 0° C., and yielded supernatants containing 28% and 12%, respectively, of the heme content of the starting material. The total yield of heme concentrate was 92%. The paste was brown and represented 85% of the protein content of the starting material.

EXAMPLE 6

A mixture of 1 ml water and 0.8 ml of 0.5 M NaOH at a temperature of +10° C. was added dropwise, while stirring, to 2.2 g of a mixture of blood cells at a temperature of +10° C. After the addition, the pH was 11.0 and the temperature +10° C. 4 ml of 96%-by-volume of ethanol, 1 ml of 2 M imidazole in 70%-by-volume ethanol, 1 ml of 30% sodium citrate in an aqueous solution and 0.5 ml of 1 M HCl were added. The pH of the mixture was 7.5 and the temperature +10° C. Hereafter 3 ml of 96%-by-volume ethanol and 10 ml of 70%-by-volume ethanol were added. The pH of the misture was 7.5, the temperature +10° C. and the ethanol content about 64%-by-volume. The mixture was centrifuged after 5 minutes as in Example 1 and yielded a supernatant containing 53% of the heme content of the starting material and a dark brown paste. The paste was extracted twice with 10 ml of 65%-by-volume ethanol and 0.1 ml of 2 M imidazole in 70%-by-volume ethanol, each time at a pH of 7.5 and a temperature of +10° C., and yielded supernatants containing 26% and 13%, respectively, of the heme content of the starting material. The total yield of heme concentrate was 92%. The paste was brown and represented 74% of the protein content of the starting material.

EXAMPLE 7

A mixture of 5.5 ml of 96%-by-volume ethanol and 1.0 ml of 1 M HCl, at a temperature of −18° C. was added dropwise, while stirring and cooling, to a mixture of 2.2 g of a mixture of blood cells, 0.1 ml of 1 M glycine in an aqueous solution, 0.1 ml of 2 M imidazole in 70%-by-volume ethanol and 2 ml of 50%-by-volume ethanol, at a temperature of −18° C. After the addition, the pH was 3.0 and the temperature −18° C. 3 ml of 40-% ammonium sulphate in an aqueous solution was added while stirring and cooling. After 5 minutes, a mixture of 10 ml of 96%-by-volume of ethanol, 20 ml of 70%-by-volume ethanol and 4 ml of 0.5 M NaOH in 70%-by-volume ethanol, at a temperature of −18° C. was added while stirring and cooling. After the addition, the pH was 7.5 and the temperature −18° C., the ethanol content was about 69% by volume. The mixture was centrifuged as in Example 1. The paste was extracted 2 times with 20 ml of 70%-by-volume ethanol, 0.1 ml of 1 M glycine in an aqueous solution and 0.1 ml of 2 M imidazole in 70-%-by-volume ethanol, each time at a pH of 7.5 and a temperature of −18° C. The supernatant contained 69%, 14% and 5%, respectively, of the heme content of the starting material. The total yield of heme concentrate was 88%. The paste was light brown and represented 81% of the protein content of the starting material.

EXAMPLE 8

A mixture of 8 ml of 96%-by-volume ethanol and 0.8 ml of 1 M HCl at a temperature of −5° C. was added dropwise, while stirring and cooling, to 2.2 g of a mixture of blood cells at a temperature of −5° C. After the addition, the pH was 3.1 and the temperature −5° C. 0.8 ml of 0.2 M NaOH in 50%-by-volume ethanol and 10 ml of 50%-by-volume ethanol were added, the pH was 3.5 and the temperature −5° C. The mixture was centrifuged at 9000×g for 5 minutes, whereby a yellow supernatant and a black paste were obtained. Out of the supernatant, after the addition of 8 ml of water, at a pH of 7.5, a grey protein precipitate containing 0.21 g of dry substance was precipitated. The black heme paste was mixed with a mixture of 30 ml of 70%-by-volume ethanol, 0.5 ml of 1 M glycine in an aqueous solution, 0.5 ml of 2 M imidazole in 70%-by-volume ethanol and 2.5 ml of 0.5 M NaOH in 70%-by-volume ethanol. The pH was 8.6, the temperature −5° C., and the ethanol content about 70% by volume. The mixture was centrifuged at 3000×g for 5 minutes and yielded a supernatant containing 72% of the heme content of the starting material and a brown paste. The paste was extracted twice with 30 ml of 70%-by-volume ethanol and 0.1 ml of 2 M imidazole in 70%-by-volume ethanol, each time at a pH of 8.6 and a temperature of −5° C., and yielded supernatants containing 19% and 8%, respectively, of the heme content of the starting material. The total yield of heme concentrate was 99%. The paste was greyish brown and weighed as dry 0.1 g. The total protein yield was 91%.

EXAMPLE 9

(a) In the same way as in Example 8, the black heme paste was separated starting from 2.2 g of a mixture of blood cells. The paste was mixed with 30 ml of 50%-by-volume ethanol and pH was adjusted to 8.5 with 0.5 M NaOH in 70%-by-volume ethanol, at a temperature of −1° C. The ethanol content was about 50%-by-volume. The mixture was centrifuged as in Example 8 and yielded a supernatant containing 33% of the heme content of the starting material and a dark brown paste. The paste was extracted 3 times with 30 ml of 50%-by-volume ethanol, each time at a pH of 9.0 and a temperature of −1° C., and yielded supernatants containing 24%, 13% and 9%, respectively, of the heme content of the starting material. The total yield of heme concentrate was 79%. The paste was brown and weighed as dry 0.1 g. The total protein yield was 91%.

(b) In the same way as in Example 8, the black heme paste was separated starting from 2.2 g of a mixture of blood cells. The paste was mixed with 30 ml of 40%-by-volume ethanol and the pH was adjusted to 10.7 with 0.5 M NaOH in 70%-by-volume ethanol. The temperature was −4° C. and the ethanol content about 40%-by-volume. The mixture was centrifuged as in Example 8 and yielded a supernatant containing 71% of the heme content of the starting material and a brown paste. The paste was extracted twice with 30 ml of 40%-by-volume ethanol, each time at a pH of 10.7 and a temperature of −4° C., and yielded supernatants containing 7.2% and 4.8%, respectively, of the heme content of the starting material. The total yield of heme concentrate was 83%. The paste was light brown and weighed as dry 0.08 g. The total protein yield was 85%.

EXAMPLE 10

In the same way as in Example 8, the black heme paste was separated starting from 2.2 g of a mixture of blood cells. The paste was mixed with a mixture of 20 ml of 60%-by-volume ethanol, 0.2 ml of 2 M imidazole in 70%-by-volume ethanol and 1 ml of 40%-by-weight of ammonium sulphate in an aqueous solution. The pH was adjusted to 6.8 with 0.5 M NaOH in 70%-by-volume ethanol. The temperature was +25° C. and the ethanol content about 60%-by-volume. The mixture was centrifuged as in Example 8 and yielded a supernatant containing 63% of the heme content of the starting material and a brownish red paste. The paste was extracted twice with 60%-by-volume ethanol, imidazole and ammonium sulphate in quantities as above, each time at a pH of 6.8 and a temperature of +25° C., and yielded supernatants containing 14% and 8%, respectively, of the heme content of the starting material. The total yield of heme concentrate was 85%. The paste was brown and weighed as dry 0.07 g. The total protein yield was 83%.

EXAMPLE 11

In the same way as in Example 8, the black heme paste was separated starting from 2.2 g of a mixture of blood cells. The paste was mixed with a mixture of 30 ml of 96%-by-volume ethanol and 0.2 ml of 1 M glycine in an aqueous solution. The pH was adjusted to 10.4 with 0.5 M NaOH in 70%-by-volume ethanol. The temperature was −20° C., the ethanol content about 90%-by-volume. The mixture was centrifuged as in Example 8 and yielded a supernatant containing 61% of the heme content of the starting material and a dark brown paste. The paste was extracted twice with 90%-by-volume ethanol and glycine in quantities as above, each time at a pH of 10.4 and a temperature of −20° C., and yielded supernatants containing 20% and 9%, respectively, of the heme content of the starting material. The total yield of heme concentrate was 90%. The paste was light brown and weighed as dry 0.1 g. The total protein yield was 91%.

EXAMPLE 12

In the same way as in Example 8, the black heme paste was separated starting from 2.2 g of a mixture of blood cells. The paste was mixed with a mixture of 30 ml of 40%-by-volume ethanol and 0.2 ml of 2 M imidazole in 70%-by-volume ethanol. The pH was adjusted to 7.0 with 0.5 NaOH in 70%-by-volume ethanol. The temperature was −5° C., the ethanol content about 42%-by-volume. The mixture was centrifuged as in Example 8 and yielded a supernatant containing 58% of the heme content of the starting material and a dark red paste. The paste was extracted 2 times with 70%-by-volume ethanol and imidazole in quantities as above, each time at a pH of 7 and a temperature of −5° C., and yielded supernatants containing 26% and 5%, respectively, of the heme content of the starting material. The total yield of heme concentrate was 89%. The paste was light brown and weighed as dry 0.1 g. The total protein yield was 91%.

EXAMPLE 13

In the same way as in Example 8, the black heme paste was separated starting from 2.2 g of a mixture of blood cells. The paste was mixed with a mixture of 20 ml of 70%-by-volume methanol and 0.2 ml of 2 M imidazole in 70%-by-volume ethanol. The pH was adjusted to 8.5 with 0.5 M NaOH in 70%-by-volume ethanol. The temperature was −5° C., the methanol content about 60%-by-volume. The mixture was centrifuged as in Example 8 and yielded a supernatant containing 67% of the heme content of the starting material and a brownish red paste. The paste was extracted twice with 70%-by-volume methanol and imidazole in quantities as above, each time at a pH of 8.5 and a temperature of −5° C., and yielded supernatants containing 18% and 7%, respectively, of the heme content of the starting material. The total yield of heme concentrate was 92%. The paste was light brown and weighed as dry 0.1 g. The total protein yield was 91%.

EXAMPLE 14

In the same way as in Example 3, the black heme paste was separated starting from 2.2 g of a mixture of blood cells. The paste was mixed with a mixture of 20 ml of 70%-by-volume propanol and 0.2 ml of 2 M imidazole in 70%-by-volume ethanol. The pH was adjusted to 8.0 with 0.5 M NaOH in 70%-by-volume ethanol. The temperature was −5° C., the propanol content about 60%-by-volume. The mixture was centrifuged as in Example 8 and yielded a supernatant containing 66% of the heme content of the starting material and a brownish red paste. The paste was extracted 2 times with 70%-by-volume propanol and imidazole in quantities as above, each time at a pH of 8.0 and a temperature of −5° C., and yielded supernatants containing 16% and 9%, respectively, of the heme content of the starting material. The total yield of heme concentrate was 91%. The paste was light brown and weighed as dry 0.1 g. The total protein yield was 91%.

EXAMPLE 15

In the same way as in Example 8, the black heme paste was separated starting from 2.2 g of a mixture of blood cells. The paste was mixed with a mixture of 20 ml of 70%-by-volume isopropanol, 0,2 ml of 1 M glycine and 0.2 ml of 2 M imidazole in 70%-by-volume ethanol. The pH was adjusted to 7.5 with 0.5 M NaOH in 70%-by-volume ethanol. The temperature was −10° C., the isopropanol content about 60%-by-volume. The mixture was centrifuged as in Example 8 and yielded a supernatant containing 69% of the heme content of the starting material and a brownish red paste. The paste was extracted twice with 70%-by-volume isopropanol, glycine and imidazole in quantities as above, each time at a pH of 7.5 and a temperature of −10° C., and yielded supernatants containing 17% and 9%, respectively, of the heme content of the starting material. The total yield of heme concentrate was 95%. The paste was light brown and weighed as dry 0.1 g. The total protein yield was 91%.

EXAMPLE 16

In the same way as in Example 8, the black heme paste was separated starting from 2.2 g of a mixture of blood cells. The paste was mixed with a mixture of 20 ml of 70%-by-volume ethanol, 7 ml of 70%-by-volume glycerine and 0.2 ml of 2 M imidazole in 70%-by-volume ethanol. The pH was adjusted to 8.0 with 0.5 M NaOH in 70%-by-volume ethanol. The temperature was −5° C., the ethanol content about 52%-by-volume and the glyserine content about 17%-by-volume. The mixture was centrifuged as in Example 8 and yielded a supernatant containing 64% of the heme content of the starting material and a brownish red paste. The paste was extracted twice with 70%-by-volume ethanol, 70%-by-volume glycerine and imidazole in quantities as above, each time at a pH of 8.0 and a temperature of −5° C., and yielded supernatants containing 14% and 7%, respectively, of the heme content of the starting material. The total yield of heme concentrate was 85%. The paste was brown and weighed as dry after washing with water 0.1 g. The total protein yield was 91%.

In the same way as above, an extraction was carried out with 70%-by-volume ethylene glycol instead of glycerine. The result was the same as above.

EXAMPLE 17

A mixture of 6 ml of 96%-by-volume ethanol and 1 ml of 1 M HCl at a temperature of −8° C. was added dropwise, while stirring and cooling, to 2.7 g of whole blood at a temperature of +0.5° C. After the addition, the pH was 3.0 and the temperature −5° C. Hereafter 2 ml of 40% ammonium sulphate in an aqueous solution and a mixture of 20 ml of 70%-by-volume ethanol, 0.2 ml of 1 M glycine in an aqueous solution and 0.2 ml of 2 M imidazole in 70%-by-volume ethanol at a temperature of −8° C. were added while stirring and cooling. The pH was adjusted to 8.0 with 0.5 M NaOH in 70%-by-volume ethanol. The temperature was −8° C. and the ethanol content about 65%-by-volume. The mixture was centrifuged as in Example 8 and yielded a supernatant containing 66% of the heme content of the starting material and a brownish red paste. The paste was extracted twice with 70%-by-volume ethanol, ammonium sulphate and imidazole in quantities as above, each time at a pH of 8.0 and a temperature of −8° C., and yielded supernatants containing 16% and 7%, respectively, of the heme content of the starting material. The total yield of heme concentrate was 89%. The paste was greyish brown after washing with 50%-by-volume ethanol and represented 85% of the total protein content.

EXAMPLE 18

An extraction of heme paste starting from 22 g of a mixture of blood cells yielded at a pH of 10.4, a temperature of −5° C. and 70%-by-volume ethanol the first extraction solution of 199 ml with the heme content of 0.38 mg heme/ml representing 68.1% of the heme content of the starting material, the second extraction solution of 121 ml with the heme content of 0.17 mg heme/ml representing 18.6% of the heme content and the third extraction solution of 118 ml, with the heme content of 0.08 mg heme/ml representing 8.5% of the heme content. The extraction solutions were combined and acidated to a pH of 5.1 with 87 ml of 0.1 M HCl, at the temperature of −5° C. The black flaky precipitate formed hereby was separated in a centrifuge at 3000×g and weighed 4.5 g. The paste was washed 3 times in 15 ml of ice water each time, suspended in 15 ml of ice water, the pH was adjusted to 8.2 with 3 ml of 0.2 M NaOH, freezed and freeze dried. Hereby 265 mg of a black powder with a heme content of 36% was obtained. The total yield of heme concentrate was 86%. Analysis: C 46.17%, H 5.30%, Cl 10.53%, P 2.8%, Fe 3.57%, N 9.6%, K 3.5% and Na 4.1%.

EXAMPLE 19

An extraction of heme paste starting from 50 g of a mixture of blood cells yielded at a pH of 8.2, a temperature of +1° C. and with 60%-by-volume ethanol and 4 ml of 2 M imidazole in 70%-by-volume ethanol the first extraction solution of 494 ml with the heme content of 0.32 heme/ml representing 62.8% of the heme content of the starting material, the second extraction solution with corresponding data 467 ml, 0.11 mg heme/ml, 20.4% and the third extraction solution with corresponding data 479 ml, 0.06 mg heme/ml, 11.4%. The extraction solutions were combined and acidated to a pH of 4.0 with 240 ml of 0.1 M HCl, at the temperature of +1° C. The precipitate was separated as above and weighed 8.5 g. The paste was washed 3 times in 25 ml of ice water each time, suspended in 25 ml of ice water, the pH was adjusted to 8.5, and the suspension was freezed and freeze dried. Hereby 510 mg of a black powder with a heme content of 42% was obtained. The total yield of heme concentrate was 85%.

EXAMPLE 20

In the same way as in Example 18, three extraction solutions were obtained. The third extraction solution was acidated separately to a pH of 5.1 and yielded a smaller amount of precipitate which, after freeze drying, yielded a heme concentrate with a heme content of 17.7%. Analysis: C 29.42%, H 3.52%, Cl 23.77%, P 1.2%, Fe 2.28%, N 8.8%, K 13.4% and Na 15.7%.

EXAMPLE 21

In the same way as in Example 19, one extraction solution was obtained. The extraction solution was acedulated separately to a pH 4.0 and yielded a black precipitate which was separated, washed and freeze dried in the same way as in Example 19. The heme concentrate thus obtained had a heme content of 55%.

I claim:

1. A method for the preparation of a heme concentrate from a mixture comprising heme and blood protein obtained by cleaving hemoglobin, said method comprising the steps of treating said mixture with a liquid comprising a dehydrating agent and having a pH of at least 8.0 to provide a supernatant and a residue; separating the residue from the supernatant; and recovering heme concentrate from the supernatant.

2. A method according to claim 1, wherein during said treating step, an agent promoting separation of heme from blood protein is included in the mixture.

3. A method according to claim 1, wherein the dehydrating agent is selected from a lower alcohol or a mixture of alcohols.

4. A method according to claim 1, wherein the treating step is performed in the presence of a solvent selected from ketones and esters.

5. A method according to claim 1, wherein the treating step is performed at a pH of from 9.0 to 10.7.

6. A method according to claim 1, wherein during said treating step, a protein precipitate stabilizing agent is included in the mixture.

7. A method according to claim 1, wherein the mixture comprising heme and blood protein comprises a heme paste obtained by cleaving hemoglobin substance and by separating the globin solution from said heme paste.

8. A method according to claim 1 or 6, wherein the protein precipitate stabilizing agent is at least one salt.

9. A method according to claim 8, wherein said salt comprises sodium, potassium or ammonium chloride, sulphate, phosphate, citrate or tartrate.

10. A method according to claim 2, wherein the agent which promotes the separation of the blood protein comprises amino acids.

11. A method according to claim 10, wherein said amino acid is selected from glycine, glutamine or lysine.

12. A method according to claim 1, wherein the pH in said mixture is first adjusted to 7 to 8, and thereafter the dehydrating agent is added.

13. A method according to claim 1, wherein at least one salt is first added to said mixture and whereafter the pH is adjusted to over 8.0.

14. A method according to claim 1, wherein the dehydrating agent is selected from the group consisting of ethanol, methanol, ethylene glycol, glycerol, propanol, isopropanol, butanol, isobutanol, and mixtures thereof.

15. A method according to claim 1, wherein the temperature is lower than 0° C.

16. A method according to claim 1, wherein the dehydrating agent is ethanol and is present in the mixture in a concentration of over 40%-by-volume.

17. A heme-containing product which contains 15 to 55% of heme prepared by the process according to claim 1, 2, 7, 11, or 12.

* * * * *

UNITED STATES PATENT AND TRADEMARK OFFICE
CERTIFICATE OF CORRECTION

PATENT NO. : 4,431,581

DATED : February 14, 1984

INVENTOR(S) : LINDROOS

It is certified that error appears in the above-identified patent and that said Letters Patent are hereby corrected as shown below:

Column 4, line 54, "$NN_4$" should read --$NH_4$--.

Column 12, line 17, "Example 3" should read --Example 8--.

Signed and Sealed this

Twenty-second Day of January 1985

[SEAL]

Attest:

DONALD J. QUIGG

Attesting Officer — Acting Commissioner of Patents and Trademarks

UNITED STATES PATENT AND TRADEMARK OFFICE
CERTIFICATE OF CORRECTION

PATENT NO. : 4,431,581
DATED : February 14, 1984
INVENTOR(S) : LINDROOS

It is certified that error appears in the above-identified patent and that said Letters Patent is hereby corrected as shown below:

Column 4, line 55, after "tartrate" add --The salt can be added first to the mixture and then the dehydrating agent is added and the pH adjusted to over 8.0.--

Column 15, line 7, after "whereafter" add --the dehydrating agent is added and--.

Signed and Sealed this

Fifteenth Day of October 1985

[SEAL]

Attest:

Attesting Officer

DONALD J. QUIGG

Commissioner of Patents and Trademarks—Designate